United States Patent [19]

Welch et al.

[11] Patent Number: 5,498,581
[45] Date of Patent: Mar. 12, 1996

[54] METHOD FOR MAKING AND USING A SUPPORTED METALLOCENE CATALYST SYSTEM

[75] Inventors: M. Bruce Welch, Bartlesville, Okla.; Helmut G. Alt; Bernd Peifer, both of Bayreuth, Germany; Syriac J. Palackal, Bartlesville, Okla.; Gary L. Glass, Dewey, Okla.; Ted M. Pettijohn, Bartlesville, Okla.; Gil R. Hawley, Dewey, Okla.; Darryl R. Fahey, Dewey, Okla.

[73] Assignee: Phillips Petroleum Company, Bartlesville, Okla.

[21] Appl. No.: 252,611

[22] Filed: Jun. 1, 1994

[51] Int. Cl.$^6$ .................................................. B01J 31/00
[52] U.S. Cl. .......................... 502/102; 502/102; 502/117; 526/129; 556/53
[58] Field of Search ........................ 502/102, 103, 502/117; 526/129; 556/53

[56] References Cited

U.S. PATENT DOCUMENTS

| | | | |
|---|---|---|---|
| 4,871,705 | 10/1989 | Hoel | 502/117 |
| 5,071,808 | 12/1991 | Antberg et al. | 502/107 |
| 5,106,804 | 4/1992 | Bailly et al. | 502/108 |
| 5,169,818 | 12/1992 | Antberg et al. | 502/159 |
| 5,240,894 | 8/1993 | Burkhardt et al. | 502/108 |
| 5,308,815 | 5/1994 | Sangokoya | 502/117 X |
| 5,308,817 | 5/1994 | Reddy et al. | 502/117 |
| 5,387,567 | 2/1995 | Tajima et al. | 502/117 X |

FOREIGN PATENT DOCUMENTS

| | | |
|---|---|---|
| 574370 | 12/1993 | European Pat. Off. . |
| 586167 | 3/1994 | European Pat. Off. . |

*Primary Examiner*—Michael Lusignan
*Attorney, Agent, or Firm*—Edward L. Bowman

[57] ABSTRACT

Methods are disclosed for preparing a highly active solid metallocene-containing catalyst system and its use in the polymerization of olefins. The catalyst system is prepared by creating a catalyst system solution by combining an aluminoxane with a metallocene having a substituent which has olefinic unsaturation in a suitable liquid to form a liquid catalyst system, conducting prepolymerization of an olefin in the liquid catalyst system, and separating the resulting solid metallocene-containing catalyst system from the reaction mixture. Also polymerization of olefins using the inventive solid catalyst system is disclosed.

38 Claims, No Drawings

METHOD FOR MAKING AND USING A SUPPORTED METALLOCENE CATALYST SYSTEM

FIELD OF THE INVENTION

This invention relates to a new type of solid particulate metallocene catalyst system useful for the polymerization and/or copolymerization of olefins. The invention is also related to a process for conducting polymerization of olefins using the inventive solid metallocene catalyst system.

BACKGROUND OF THE INVENTION

The term "Metallocene" as used herein refers to a derivative of cyclopentadienylidene which is a metal derivative containing at least one cyclopentadienyl component which is bonded to a transition metal. The transition metal is selected from Groups IVB, VB, and VIB, preferably IVB and VIB. Examples include titanium, zirconium, hafnium, chromium, and vanadium. A number of metallocenes have been found to be useful for the polymerization of olefins. Generally, the more preferred catalysts are metallocenes of Zr, Hf, or Ti.

Generally, in order to obtain the highest activity from metallocene catalysts, it has been necessary to use them with an organoaluminoxane cocatalyst, such as methylaluminoxane. This resulting catalyst system is generally referred to as a homogenous catalyst system since at least part of the metallocene or the organoaluminoxane is in solution in the polymerization media. These homogenous catalysts systems have the disadvantage that when they are used under slurry polymerization conditions, they produce polymer which sticks to reactor walls during the polymerization process and/or polymer having small particle size and low bulk density which limits the commercial utility.

Some attempts to overcome the disadvantages of the homogenous metallocene catalyst systems are disclosed in U.S. Pat. Nos. 5,240,894, 4,871,705; and 5, 106,804. Typically, these procedures have involved the prepolymerization of the metallocene aluminoxane catalyst system either in the presence of or in the absence of a support. An evaluation of these techniques has revealed that there is still room for improvement, particularly when the catalyst is one which is to be used in a slurry type polymerization where the object is to produce a slurry of insoluble particles of the end product polymer rather than a solution of polymer which could result in fouling of the reactor. In the operation of a slurry polymerization in a continuous loop reactor it is extremely important for efficient operations to limit polymer fouling of the internal surfaces of the reactor. The term "fouling" as used herein refers to polymer buildup on the surfaces inside the reactor.

An object of the present invention is to provide a new method for preparing a solid metallocene catalyst system. In accordance with another aspect of the present invention, there is provided a method for polymerizing olefins using the new type of prepolymerized metallocene.

SUMMARY OF THE INVENTION

In accordance with the present invention, a solid particulate metallocene-containing catalyst system is produced by (a) combining an organoaluminoxane and at least one metallocene having at least one cyclopentadienyl-type ligand having at least one olefinic unsaturated substituent in a liquid to form a liquid catalyst system, (b) conducting prepolymerization of at least one olefin in the presence of said liquid catalyst system, to produce a prepolymerized solid catalyst, and (c) separating the resulting solid from the liquid and the components dissolved in the liquid, said solid being the solid particulate metallocene catalyst system. The phrase "liquid catalyst system" as used herein refers to the combination of the aluminoxane, the metallocene, and the liquid, irrespective of whether the aluminoxane and/or the metallocene are dissolved in the liquid.

In accordance with another aspect of the present invention, the resulting inventive solid particulate metallocene-containing catalyst system is employed in the polymerization of an olefin by contacting the olefin with the inventive solid particulate metallocene-containing catalyst system under suitable reaction conditions.

DETAILED DESCRIPTION OF THE INVENTION

A wide range of metallocenes are considered to be applicable to the present process. The essential feature is that the metallocene be one wherein at least one cyclopentadienyl-type ligand has a substituent having a polymerizable olefinic group. Some examples of such olefin-containing metallocenes are disclosed in U.S. Pat. No. 5,169,818 and published European Application No. 574,370. The invention is considered applicable to both bridged and unbridged metallocenes. The unbridged metallocenes can even include bridged ligands which contain two cyclopentadienyl-type radicals connected by a suitable bridging structure but wherein only one of the cyclopentadienyl-type radicals of that ligand is bonded to the transition metal. Alternatively the olefinic substituent can be on the bridge connecting the two cyclopentadienyl-type groups.

The metallocenes of the type contemplated as useful for the present invention include those represented by the formula $R_x(Z)(Z)MeQ_k$ wherein each Z bound to Me and is the same or different and is a cyclopentadienyl-type ligand selected from substituted or unsubstituted cyclopentadienyl, indenyl, tetrahydroindenyl, octahydrofluorenyl, and fluorenyl ligands; R is a structural bridge linking the Z's and Me is a metal selected from the group consisting of IVB, VB, and VIB metals of the periodic table, each Q is the same or different and is selected from the group consisting of hydrogen, halogens, and organoradicals; x is 1 or 0; k is a number sufficient to fill out the remaining valances of Me; further characterized by the fact that it has at least one olefinically unsaturated substituent attached. In bridged metallocenes this olefinically unsaturated substituent can be a branch on the bridging unit or on one or both of the cyclopentadienyl-type groups of the bridged ligands.

A particularly preferred type of bridged metallocene includes those in which the olefinically unsaturated substituent has the formula

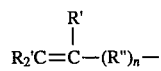

wherein R" is a hydrocarbyl diradical having 1 to 20 carbon atoms; more preferably 2 to 10; n is 1 or 0, and each R' is individually selected from the group consisting of organo radicals having 1 to 10 carbon atoms and hydrogen. Most preferably R" has at least two carbons in its main alkylene chain, i.e. it is a divalent ethylene radical or a higher homolog thereof.

Some olefinic branched bridged ligands useful for making metallocenes suitable for the present invention can be prepared by reacting a dihalo olefinic compound with an alkali metal salt of a suitable cyclopentadienetype compound to produce a compound of the formula Z—R—Z where R is a bridge having olefinic unsaturation and wherein each Z is the same or alternatively to first produce a compound of the formula Z—R—X wherein X is a halogen and then reacting that compound with an alkali metal salt of another different cyclopentadiene-type compound to produce a compound of the formula Z—R—Z wherein the two Z's differ. Such reactions can be carried out using conditions of the type disclosed in U.S. Pat. No. 5,191,132.

An alternate technique for forming an olefinic branched bridged ligand involves reacting a carbonyl compound having olefinic unsaturation with a cyclopentadiene-type compound in the presence of a base and methanol to yield an alkenyl fulvene which is then reacted with an alkali metal salt of a cyclopentadiene-type compound, such as, for example, fluorene, to yield the unsaturated-branched-bridged ligand containing two cyclopentadienyl-type groups, i.e. fluorenyl and cyclopentadienyl. For example, one could react 5-hexene-2-one with cyclopentadiene using a procedure like that disclosed by Stone et al in *J. Org. Chem.*, 49, 1849 (1984) to yield 6-(but-3-enyl)-6-methyl-fulvene which could then be reacted with fluorenyllithium and subsequently hydrolyzed to yield 5-cyclopentadienyl-5-(9-fluorenyl)-1-hexene, also sometimes referred to as 1-(9-fluorenyl)-1-(cyclopentadienyl)-1-(methyl)-1-(but-3-enyl) methane.

The present invention thus envisions using bridged metallocenes prepared from vinyl terminated branched bridged ligands of the formula

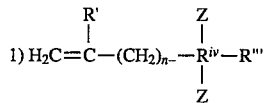

wherein n is a number typically in the range of about 0 to 20; more preferably 2–10; $R^{iv}$ is Si, Ge, C, or Sn; R''' and R'' are each individually selected from hydrogen, or organo groups having 1 to 10 carbons. Currently preferred R' and R''' components are hydrogen or alkyl groups typically having 1 to 10 carbon atoms, or aryl groups typically having 6 to 10 carbon atoms. Z is a cyclopentadienyl-type radical as described earlier.

The metallocenes of such olefinically unsaturated branched-bridged ligands can be prepared by reacting the olefinically branched-bridged bis(cyclopentadienyl-type) ligand with an alkali metal alkyl to produce a divalent ligand salt that is then reacted with the transition metal compound to yield the metallocene, using the techniques generally known in the art for forming such metallocenes. See, for example, the technique disclosed in European Published Application 524,624, the disclosure of which is incorporated herein by reference.

Some typical examples of some metallocenes containing a substituent having olefinic unsaturation include 5-(cyclopentadienyl)-5-(9-fluorenyl)1-hexene zirconium dichloride, bis(9-fluorenyl)(methyl)(vinyl)silane zirconium dichloride, bis(9-fluorenyl)(methyl)(prop-2-enyl)silane zirconium dichloride, bis(9-fluorenyl) (methyl)(but-3-enyl)silane zirconium dichloride, bis(9-fluorenyl)(methyl) (hex-5-enyl) silane zirconium dichloride, bis( 9-fluorenyl)(methyl) (oct-7-enyl)silane zirconium dichloride, (cyclopentadienyl)(1-allylindenyl) zirconium dichloride, bis(1-allylindenyl) zirconium dichloride, (9-(prop-2-enyl)fluorenyl)(cyclopentadienyl)zirconium dichloride, (9-(prop-2-enyl)fluorenyl)(pentamethylcyclopentadienyl)zirconium dichloride, bis(9-(prop-2-enyl)fluorenyl) zirconium dichloride, (9-(cyclopent-2-enyl) fluorenyl)(cyclopentadienyl) zirconium dichloride, bis( 9-(cyclopent-2-enyl) (fluorenyl) zirconium dichloride, 5-(2-methylcyclopentadienyl)-5-(9-fluorenyl)-1-hexene zirconium dichloride, 5-(fluorenyl)-5-(cyclopentadienyl)-1-hexene hafnium dichloride, (9-fluorenyl)(1-allylindenyl)dimethylsilane zirconium dichloride, 1-(2,7-di(alphamethylvinyl)(9-fluorenyl))-1-(cyclopentadienyl)-1,1-dimethylmethane zirconium dichloride, 1-(2,7-di(cyclohex-1-enyl)(9-fluorenyl))-1-(cyclopentadienyl)- 1,1-methane zirconium dichloride, 5-(cyclopentadienyl)-5-(9-fluorenyl)-1-hexene titanium dichloride, and the like.

These various metallocenes can be prepared by reacting the necessary cyclopentadienyl-type alkali metal salt with a transition metal compound. Some examples of such reactions are disclosed in the aforementioned published EPC application no. 524,624.

The organo aluminoxane component used in preparing the inventive solid catalyst system is an oligomeric aluminum compound having repeating units of the formula

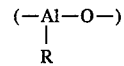

Some examples are often represented by the general formula $(R-Al-O)_n$ or $R(R-Al-O-)_n AlR^2$. In the general alumoxane formula R is a $C_1$–$C_5$ alkyl radical, for example, methyl, ethyl, propyl, butyl or pentyl and "n" is an integer from 1 to about 50. Most preferably, R is methyl and "n" is at least 4. Aluminoxanes can be prepared by various procedures known in the art. For example, an aluminum alkyl may be treated with water dissolved in an inert organic solvent, or it may be contacted with a hydrated salt, such as hydrated copper sulfate suspended in an inert organic solvent, to yield an aluminoxane. Generally the reaction of an aluminum alkyl with a limited amount of water is postulated to yield a mixture of the linear and cyclic species of the aluminoxane.

In the first step of the present invention, the metallocene and aluminoxane are combined in the presence of a suitable liquid to form a liquid catalyst system. It is preferred that the liquid catalyst system be prepared using an organic liquid in which the aluminoxane is at least partially soluble. The currently preferred liquids are hydrocarbons such as hexane or toluene. Typically some aromatic liquid solvent is employed. Examples include benzene, toluene, ethylbenzene, diethylbenzene, and the like. The amount of liquid to be employed is not particularly critical. Nevertheless, the amount should preferably be such as to dissolve the product of the reaction between the metallocene and the aluminoxane, provide desirable polymerization viscosity for the prepolymerization, and to permit good mixing. The temperature is preferably kept below that which would cause the metallocene to decompose. Typically the temperature would be in the range of −50° C. to 100° C. Preferably, the metallocene, the aluminoxane, and the liquid diluent are combined at room temperature, i.e. around 10° to 30° C. The reaction between the aluminoxane and the metallocene is relatively rapid. The reaction rate can vary depending upon the ligands of the metallocene. It is generally desired that they be contacted for at least about a minute to about 1 hour.

It is within the scope of the invention to form the liquid catalyst system in the presence of a particulate solid. Any number of particulate solids can be employed as the particulate solid. Typically the support can be any organic or inorganic solid that does not interfere with the desired end result. Examples include porous supports such as talc, inorganic oxides, and resinous support materials such as particulate polyolefins. Examples of inorganic oxide materials include Groups II, III, IV or V metal oxides such as silica, alumina, silica-alumina, and mixtures thereof. Other examples of inorganic oxides are magnesia, titania, zirconia, and the like. Other suitable support materials which can be employed include such as, magnesium dichloride, and finely divided polyolefins, such as polyethylene. It is within the scope of the present invention to use a mixture of one or more of the particulate solids.

It is generally desirable for the solid to be thoroughly dehydrated prior to use, preferably it is dehydrated so as to contain less than 1% loss on ignition. Thermal dehydration treatment may be carried out in vacuum or while purging with a dry inert gas such as nitrogen at a temperature of about 20° C. to about 1000° C., and preferably, from about 300° C. to about 800° C. Pressure considerations are not critical. The duration of thermal treatment can be from about 1 to about 24 hours. However, shorter or longer times can be employed provided equilibrium is established with the surface hydroxyl groups.

Dehydration can also be accomplished by subjecting the solid to a chemical treatment in order to remove water and reduce the concentration of surface hydroxyl groups. Chemical treatment is generally capable of converting all water and hydroxyl groups in the oxide surface to relatively inert species. Useful chemical agents are for example, trimethylaluminum, ethyl magnesium chloride, chlorosilanes such as $SiCl_4$, disilazane, trimethylchlorosilane, dimethylaminotrimethylsilane and the like.

The chemical dehydration can be accomplished by slurrying the inorganic particulate material such as, for example silica, in an inert low boiling hydrocarbon, such as for example, hexane. During the chemical dehydration treatment, the silica should be maintained in a moisture and oxygen free atmosphere. To the silica slurry is then added a low boiling inert hydrocarbon solution of the chemical dehydrating agent, such as, for example dichloroldimethylsilane. The solution is added slowly to the slurry. The temperature ranges during chemical dehydration reaction can be from about 20° C. to about 120° C., however, higher and lower temperatures can be employed. Preferably, the temperature will be about 50° C. to about 100° C. The chemical dehydration procedure should be allowed to proceed until all the substantially reactive groups are removed from the particulate support material as indicated by cessation of gas evolution. Normally, the chemical dehydration reaction will be allowed to proceed from about 30 minutes to about 16 hours, preferably, 1 to 5 hours. Upon completion of the chemical dehydration, the solid particulate material may be filtered under a nitrogen atmosphere and washed one or more times with a dry, oxygen free inert solvent. The wash solvents as well as the diluents employed to form the slurry and the solution of chemical dehydrating agent, can be any suitable inert hydrocarbon. Illustrative of such hydrocarbons are pentane, heptane, hexane, toluene, isopentane and the like.

Another chemical treatment that can be used on solid inorganic oxides such as silica involves reduction by contacting the solid with carbon monoxide at an elevated temperature sufficient to convert substantially all the water and hydroxyl groups to relatively inactive species.

The specific particle size of the support or inorganic oxide, surface area, pore volume, and number of hydroxyl groups is not considered critical to its utility in the practice of this invention. However, such characteristics often determine the amount of support to be employed in preparing the catalyst compositions, as well as affecting the particle morphology of polymers formed. The characteristics of the carrier or support must therefore be taken into consideration in choosing the same for use in the particular invention.

It is also within the scope of the present invention to add such a particulate solid to the liquid catalyst system after it has been formed and to carryout the prepolymerization in the presence of that solid.

The amount of aluminoxane and metallocene used in forming the liquid catalyst system for the prepolymerization can vary over a wide range. Typically, however, the molar ratio of aluminum in the aluminoxane to transition metal of the metallocene is in the range of about 1:1 to about 20,000:1, more preferably, a molar ratio of about 50:1 to about 2000:1 is used. If a particulate solid, i.e. silica, is used generally it is used in an amount such that the weight ratio of the metallocene to the particulate solid is in the range of about 0.00001/1 to 1/1, more preferably 0.0005/1 to 0.2/1.

The prepolymerization is conducted in the liquid catalyst system, which can be a solution, a slurry, or a gel in a liquid. A wide range of olefins can be used for the prepolymerization. Typically, the prepolymerization will be conducted using an olefin, preferably selected from ethylene and non-aromatic alpha-olefins, and as propylene. It is within the scope of the invention to use a mixture of olefins, for example, ethylene and a higher alpha olefin can be used for the prepolymerization. The use of, a higher alpha olefin, such as 1-butene, with ethylene is believed to increase the amount of copolymerization occurring between the olefin monomer and the olefinically unsaturated portion of the metallocene.

The prepolymerization can be conducted under relatively mild conditions. Typically, this would involve using low pressures of the olefin and relatively low temperatures designed to prevent site decomposition resulting from high concentrations of localized heat. The prepolymerization typically occurs at temperatures in the range of about −15° C. to about +110° C., more preferably in the range of about +10° to about +30° C. The amount of prepolymer can be varied but typically would be in the range of from about 1 to about 95 wt % of the resulting prepolymerized solid catalyst system, more preferably about 5 to 80 wt %. It is generally desirable to carry out the prepolymerization to at least a point where substantialy all of the metallocene is in the solid rather than in the liquid since that maximizes the use of the metallocene.

After the prepolymerization, the resulting solid prepolymerized catalyst is separated from the liquid of the reaction mixture. Various techniques known in the art can be used for carrying out this step. For example, the material could be separated by filtration, decantation, or by vacuum evaporation. It is currently preferred, however, not to rely upon vacuum evaporation since it is considered desirable to remove substantially all of the soluble components in the liquid reaction product of the prepolymerization from the resulting solid prepolymerized catalyst before it is stored or used for subsequent polymerization. After separating the solid from the liquid, the resulting solid is preferably washed with a hydrocarbon and then dried using high vacuum to remove substantially all the liquids and other volatile components that might still be associated with the solid. The vacuum drying is preferably carried out under relatively mild conditions, i.e. temperatures below 100° C. More typically the prepolymerized solid is dried by subjection to a high vacuum at a temperature of about 30° C. until a substantially constant weight is achieved. A preferred technique employs at least one initial wash with an aromatic hydrocarbon, such as toluene, followed by a wash with a parafinic hydrocarbon, such as hexane, and then vacuum drying.

It is within the scope of the present invention to contact the prepolymerization reaction mixture product with a liquid in which the prepolymer is sparingly soluble, i.e. a countersolvent for the prepolymer, to help cause soluble prepolymer to precipitate from the solution. Such a liquid is also useful for the subsequent washing of the prepolymerized solid.

It is also within the scope of the present invention to add a particulate solid of the type aforementioned after the prepolymerization. Thus one can add the solid to the liquid prepolymerization product before the countersolvent is added. In this manner soluble prepolymer tends to precipitate onto the surface of the solid to aid in the recovery of the filtrate in a particulate form and to prevent agglomeration during drying. The liquid mixture resulting from the prepolymerization or the inventive solid prepolymerized catalyst can be subjected to sonification to help break up particles if desired.

Further, if desired the recovered solid prepolymerized catalyst system can be screened to give particles having sizes that meet the particular needs for a particular type of polymerization.

Another option is to combine the recovered inventive solid prepolymerized catalyst system with an inert hydrocarbon, such as one of the type used as a wash liquid, and then to remove that liquid using a vacuum. In such a process it is sometimes desirable to subject the resulting mixture to sonification before stripping off the liquid.

The resulting solid prepolymerized metallocene-containing catalyst system is useful for the polymerization of olefins. Generally, it is not necessary to add any additional aluminoxane to this catalyst system. In some cases it may be found desirable to employ small amounts of an organoaluminum compound as a scavenger for poisons. The term organoaluminum compounds include compounds such as triethylaluminum, trimethylaluminum, diethylaluminum chloride, ethylaluminum dichloride, ethylaluminum sesquichloride, and the like. Trialkyl aluminum compounds are currently preferred. Also in some applications it may be desirable to employ small amounts of antistatic agents which assist in preventing the agglomeration of polymer particles during polymerization. Still further, when the inventive catalyst system is added to a reactor as a slurry in a liquid, it is sometimes desirable to add a particulate dried solid as a flow aid for the slurry. Preferably the solid has been dried using one of the methods described earlier. Inorganic oxides such as silica are particularly preferred. Currently, it is preferred to use a fumed silica such as that sold under the tradename Cab-o-sil. Generally the fumed silica is dried using heat and trimethylaluminum.

The solid catalyst system is particularly useful for the polymerization of alpha-olefins having 2 to 10 carbon atoms. Examples of such olefins include ethylene, propylene, butene-1, pentene-1, 3-methylbutene-1, hexene- 1,4-methylpentene- 1,3-methylpentene- 1, heptene- 1, octene- 1, decene- 1, 4,4-dimethyl-1-pentene, 4,4-diethyl-1-hexene, 3,4-dimethyl-1-hexene, and the like and mixtures thereof. The catalysts are also useful for preparing copolymers of ethylene and propylene and copolymers of ethylene or propylene and a higher molecular weight olefin.

The polymerizations can be carried out under a wide range of conditions depending upon the particular metallocene employed and the particular results desired. Although the inventive catalyst system is a solid, it is considered that it is useful for polymerization conducted under solution, slurry, or gas phase reaction conditions.

When the polymerizations are carried out in the presence of liquid diluents obviously it is important to use diluents which do not have an adverse effect upon the catalyst system. Typical liquid diluents include propane, butane, isobutane, pentane, hexane, heptane, octane, cyclohexane, methylcyclohexane, toluene, xylene, and the like. Typically the polymerization temperature can vary over a wide range, temperatures typically would be in a range of about −60° C. to about 300° C., more preferably in the range of about 20° C. to about 160° C. Typically the pressure of the polymerization would be in the range of from about 1 to about 500 atmospheres or even greater. The inventive catalyst system is particularly useful for polymerizations carried out under particle form, i.e., slurry-type polymerization conditions.

The polymers produced with this invention have a wide range of uses that will be apparent to those skilled in the art from the physical properties of the respective polymers. Applications such as molding, films, adhesives, and the like are indicated.

A further understanding of the present invention, its various aspects, objects and advantages will be provided by the following examples.

Example I

In this synthesis 20.6 mL of cyclopentadiene and 11.7 mL of 5-hexene-2-one were dissolved in 100 mL of methanol. While cooling in ice 12.4 mL of pyrrolidine was added and the reaction mixture was stirred overnight at room temperature. Then 9.6 mL of glacial acetic acid was added. The reaction mixture was stirred for one half hour and then the solvent was evaporated in a vacuum. The residue was dissolved in 200 mL of diethyl ether and washed five times with 100 mL of water. The organic phase was filtered using a silica gel and dried over sodium sulfate. The solvent was evaporated in a vacuum. A yellow oil was recovered which was identified as 6-(3-butenyl)-6-methylfulvene.

A solution was prepared by dissolving 10 g of fluorene in 100 mL of THF and then this was slowly reacted with 37.6 mL of a 1.6 molar solution of n-butyllithium in hexane. This dark red solution was stirred overnight at room temperature. Then a solution was prepared by combining 8.8 g of 6-(butenyl)-6-methylfulvene with 50 mL of THF. This later solution was then added dropwise over a period of one half hour to the solution of the fluorenyl lithium salt. The resulting reaction mixture was stirred overnight at room temperature and then 100 mL of water was added. The organic phase was dried overnight over sodium sulfate and the solvent was evaporated in a vacuum. The yellow residue was dissolved in pentane and filtered using silica gel. The solvent was concentrated by means of evaporation. Crystallization took place at about −18° C. to give 5-(cyclopentadienyl)-5-(9-fluorenyl)-1-hexene in the form of a white solid. This compound is also sometimes referred to as 1-(9-fluorenyl)-1-(cyclopentadienyl)-1-(but-3-enyl)-1-(methyl) methane.

Example II

Five grams of compound 5-(cyclopentadienyl)-5-(9-fluorenyl)-1-hexene was reacted with twice as many moles of n-butyllithium in 100 mL diethylether using conditions of the type taught in published European Patent Appln. No. 524,624 to produce the divalent ligand salt. The divalent ligand salt in diethyl ether was then reacted with 3.96 grams of zirconium tetrachloride at room temperature. The orange metallocene 1-(9-fluorenyl)- 1-cyclopentadienyl)-1-(but-3- enyl)-1-(methyl) methane zirconium dichloride was recovered and purified by decanting off the liquid and recrystallization in dichloroethane at −18° C. Then the liquid was decanted off and the solid dried using a high vacuum.

The effectiveness of this metallocene for the polymerization of ethylene was evaluated. A comparative polymerization technique involved combining a selected amount of the metallocene with a 1.1 molar solution of methylaluminoxane (MAO) in toluene obtained from Schering. This resulting catalyst system solution (Catalyst A) was then injected into an autoclave. The autoclave was then filled with 2 liters of isobutane and the temperature was raised to about 90° C., the polymerization temperature. Then hydrogen was added from a 300 cc vessel in an amount equal to a 10 psi pressure drop in the vessel and then the reactor was then pressurized to 450 psig with ethylene. The polymerization was continued for one hour after reaching the 90° C. reaction temperature. Then the reactor was cooled and vented and the solid polymer was recovered.

In another series of runs, a number of inventive solid catalyst systems were prepared by combining the metallocene and the methylaluminoxane toluene solution to produce a liquid catalyst system which was then contacted with ethylene under prepolymerization conditions to produce a solid prepolymerized catalyst system. Specifically, 19.3 mL of a 1.1 molar toluene solution of methylaluminoxane with 0.102 gms of the metallocene to result in the liquid catalyst solution. A first solid catalyst system was prepared by adding 2 mL of that solution to 38 mL of toluene; then ethylene was bubbled through the solution for 105 min at room temperature to effect prepolymerization. Then 40 mL of hexane was added to the mixture and the resulting mixture was filtered. The resulting solid was then washed with 10 mL of hexane and dried. The drying involved subjecting the recovered powder to a high vacuum for one hour.

A second solid inventive catalyst was prepared by combining 2 mL of the liquid catalyst solution with 32 mL of toluene and 6 additional ml of the Schering methylaluminoxane solution. The prepolymerization and recovery of the solid catalyst was carried out in the same manner as before.

A third inventive solid prepolymerized catalyst was prepared by combining 2 mL of the liquid catalyst solution with 26 mL of toluene and an additional 12 mL of the commercial Schering methylaluminoxane solution. The prepolymerization and recovery of the solid prepolymerized catalyst was as described for the first inventive catalyst.

Still another inventive catalyst system was prepared by combining 2 mL of the liquid catalyst solution with 20 mL of toluene and an additional 18 mL of the commercial methylaluminoxane solution. Again, the prepolymerization and recovery of this inventive solid catalyst system was as described before.

Still another inventive catalyst system was prepared by combining 2 mL of the liquid catalyst solution with 38 mL of the commercial methylaluminoxy toluene solution. Again the prepolymerization and isolation of the inventive catalyst was carried as described before.

All of these inventive prepolymerized solid catalyst systems were then evaluated for the polymerization of ethylene. In these runs, a hexane slurry of the solid prepolymerized catalyst was subjected to sonification and then added to the reactor which was then filled with isobutane. Hydrogen was added as was done in the comparative run. The reactor was then pressurized with ethylene and the temperature raised to conduct the prepolymerization as done in the comparative run. A comparison of the variables involved and the results obtained are set forth in the following table.

TABLE I

| Catalyst | Molar Ratio Al/Zr | gPE/g Catalyst/Hr | Melt Index | HLMI/MI | Fouling |
|---|---|---|---|---|---|
| A (Solution) | 965 | 1170 | 0.43 | 41 | 10 |
| 1 | 100 | 6880 | 0.91 | 20 | 1 |
| 2 | 400 | 836 | 0.65 | 19 | 1 |
| 3 | 700 | 9840 | 0.93 | 17 | 1 |
| 4 | 1000 | 5970 | 0.67 | 21 | 1 |
| 5 | 2000 | 7230 | 0.74 | 19 | 3 |

The results demonstrate that the inventive solid prepolymerized catalyst system over a wide range of aluminum to zirconium ratios was more active than the soluble catalyst system of the comparative run. The productivity of catalyst 2 is considered anomalous. In addition, the polymerization carried out using the soluble catalyst system produced substantial amounts of fouling, the number 10 indicating that there was severe fouling of the reactor which required a heated solvent wash for removing the adhered polymer. The value of 1 under the heading "Fouling" indicates that there was no visible indication of fouling. The number 3 under the heading "Fouling" indicates that there was a slight amount of fouling but that it was easily removed from the reactor without requiring a heated solvent wash. Accordingly, the inventive catalysts were capable of being used in slurry polymerization without causing significant fouling of the reactor. It has further been observed that the inventive catalysts produce a polymer that has a higher bulk density than the polymers produced using a catalyst solution such as that used in the comparative run. It has further been observed that the polymers produced with the inventive solid prepolymerized catalyst have a much lower density than one would expect for the melt index observed, especially when no comonomer was used. Still further, NMR analysis of polymers made with the inventive solid prepolymerized catalyst systems reveal that the polymers contain ethyl branches. This all leads to the conclusion that something quite different than ordinary ethylene homopolymerization is occurring when this inventive prepolymerized catalyst is employed. Specifically it indicates that a copolymer-like product is being obtained even though no comonomer was employed.

Example III

A series of tests were made to compare the inventive procedure to a procedure in which a prepolymerization is conducted but on a similar metallocene which did not contain a branch having olefinic unsaturation. In this case, the metallocene was 1-(9-fluorenyl)-1-(cyclopentadienyl)-1-(methyl)-1-(butyl)methane zirconium dichloride. The ligand and metallocene were prepared in a manner like that explained in Example I but using 6-butyl-6-methyl fulvene rather than the butenyl fulvene. Thus, the only difference between this metallocene and that used in the preceding example was that the hydrocarbon branch on the bridge in this example did not have olefinic unsaturation. In a first run, a solution of 0.007 grams of the metallocene and 10 mL of a 1.1M Schering methylaluminoxane toluene was prepared and that catalyst solution was employed without prepolymerization. It is referred to as catalyst solution B. Also, three prepolymerized solid catalyst systems were prepared using a catalyst system solution prepared from the same metallocene and MAO to obtain solid prepolymerized catalysts of varying aluminum to zirconium ratios. In this case the catalyst solution was prepared by combining 19.3 mL of the 1.1M Schering MAO toluene solution with 0.1 grams of the butyl-substituted bridged metallocene.

The first comparative solid prepolymerized catalyst system C was prepared by combining 2 mL of the butyl metallocene/MAO catalyst system solution with an additional 38 mL of the methylaluminoxane solution. After refrigerating for 24 hours, ethylene was bubbled through this solution for 105 min at room temperature. The net weight gain was 1.6 gm. While stirring, 40 mL of n-hexane was added to the mixture. The mixture was then filtered and washed with 10 mL of n-hexane and dried under a high vacuum for one hour.

A second comparative solid catalyst system D was prepared by combining 2 mL of the butyl catalyst system solution with 20 mL of toluene and an additional 18 mL of the methylaluminoxane toluene solution. The prepolymerization was conducted in the same manner and the solid was separated and dried in the same manner.

Still yet another comparative solid catalyst system E was prepared by combining 2 mL of the butyl catalyst system solution with 26 mL of toluene and 12 additional mL of the methylaluminoxane solution. The prepolymerization, recovery and drying were carried out as before.

A comparison of the variables and the results obtained are set forth in the following table.

TABLE II

| Catalyst | Molar Ratio Al/Zr | PEg/g Catalyst/Hr | Melt Index | HLMI/M | Fouling |
|---|---|---|---|---|---|
| B (Solution) | 750 | 417 | (0.38 HLMI) | NA | 10 |
| C | 1900 | 32 | 0 | NA | 8 |
| D | 1000 | 85 | 0 | NA | 8 |
| E | 600 | 107 | 0 | NA | 8 |

In this case, the prepolymerized solid catalyst system did not appear to be more active than the solution type catalyst system. Further, it will be noted that while the prepolymerized catalysts produce somewhat less fouling than the solution catalyst system, the fouling was still significantly much higher than that obtained with the butenyl prepolymerized inventive solid catalyst system of Example II.

Example IV

This example deals with preparing the inventive solid catalyst system in the presence of an inorganic support.

The support employed was a silica sold as Davidson Grade 948. It had an average particle size of 50 micron. It was dried in a muffle furnace. The temperature was increased about 200° C. per hour in the muffle furnace until 800° C. was reached. The resulting solid was then cooled and placed in a 800 mL flask and covered with dried n-hexane. The resulting mixture was then stirred while 160 mL of a 14.5 weight percent solution of trimethylaluminum in n-heptane was added in about 20 mL increments. After all the trimethylaluminum solution had been added, the slurry was stirred for about two additional hours. Then a solution of 0.06 gm of Stadis 450 in 50 mL of toluene was added. The slurry was then allowed to settle and the solvent was decanted. The solid was then washed three times with 180 mL portions of dried n-hexane. The liquid was decanted and the solid was left to stand overnight. Then the solid was dried under a vacuum.

This dried silica was then employed in the preparation of the inventive solid catalyst system. In a glove box, 0.275 gm of 1-(9-fluorenyl)- 1-(cyclopentadienyl)-1-(methyl)-1-(but-3-enyl) methane zirconium dichloride was placed in a 800 mL flask. Then 180 mL of a 1.1 molar methylaluminoxane toluene solution obtained from Schering and 340 mL of toluene were added to the flask. The mixture was stirred and ethylene was bubbled through it for one hour at room temperature. Then 47 gm of the dried silica was added. The mixture was again stirred and ethylene was bubbled through the mixture for an additional hour. The resulting weight gain was 7.09 gm. Ethylene was then bubbled through the stirred mixture for one additional hour. The weight gain overall was 12.58 gm. The resulting solid was separated from the liquid by filtering and was washed twice with 140 mL of toluene and twice with 140 mL of dried n-hexane. Although the recovered solid appeared to be a powder, it was still considered to contain some liquid. A portion of this liquid-containing catalyst was evaluated for the polymerization of ethylene. Another portion of the liquid-containing catalyst system was subjected to drying for one hour using a membrane pump and then two hours under a vacuum of about 1 mm of mercury. The resulting dry catalyst was then also evaluated for the polymerization of ethylene.

In these two polymerizations, the solid catalyst system was added to the autoclave as a powder rather than as a slurry of the powder in a liquid diluent. Otherwise the polymerizations were as described for the preceding examples. Both catalysts produced polyethylene with minimal fouling of the reactor. The fouling rated a 1 value. The aluminum-to-zirconium ratio used to prepare the solid catalyst in the polymerization in both cases was 350. The wet catalyst system had a productivity of 900 gm of polymer per gram of catalyst, wherein the silica was included as part of the catalyst weight. The dried catalyst system had a productivity of 4,800 gm of polymer per gram of catalyst, again wherein the silica was included in the weight of the catalyst. This is a particularly unusual activity since silica is generally viewed as an inert diluent which adds nothing to the activity of a prepolymerized catalyst.

Example V

A number of other metallocenes containing a substituent having olefinic unsaturation were also used to prepare catalysts according to the present invention. Among the metallocenes employed were: (cyclopentadienyl)(9-(prop-2-enyl)fluorenyl) zirconium dichloride (cyclopentadienyl)(9-(cyclopent-2-enyl)fluorenyl) zirconium dichloride 1-(1-allylindenyl)-1-(9-fluorenyl)-1-(dimethyl) silane zirconium dichloride (di(9-fluorenyl) (hex-5-enyl) methyl silane zirconium dichloride di(9-fluorenyl) (prop-2-enyl) (methyl vinyl) silane zirconium dichloride In all cases, when the prepolymerized inventive solid catalyst systems were employed in the slurry polymerization of ethylene, they produced less fouling than was observed for the solution type controls of Examples I and III. With the exception of the inventive catalyst system made from di(9-fluorenyl) (prop-2-enyl) methyl silane zirconium dichloride, the fouling observed was much lower than that observed for any of the catalysts employed in Example III. Additional study would be needed to determine why that particular propenyl methyl silane zirconium dichloride did not perform as well as the other olefin-substituted metallocenes.

That which is claimed is:

1. A method for preparing a solid metallocene-containing catalyst system comprising (a) combining in a liquid an organoaluminoxane and at least one metallocene having at least one cyclopentadienyl, indenyl, tetrahydroindenyl, octahydrofluorenyl, or fluorenyl ligand having at least one olefinically unsaturated substituent to form a liquid catalyst system, (b) conducting prepolymerization of at least one olefin in the presence of said catalyst system to produce a prepolymerized solid catalyst containing no more than about 95 weight percent prepolymer, and (c) separating the resulting solid from the liquid and components dissolved in said liquid.

2. A method according to claim 1 wherein after the solid is separated from the liquid in step (c) the solid is subjected to drying to remove substantially all the liquid.

3. A method according to claim 2 wherein an aromatic solvent is used for forming the liquid catalyst system.

4. A method according to claim 3, wherein the solvent that is used for forming the liquid catalyst system is toluene.

5. A method according to claim 4, wherein a solid particulate support is added to the reaction product of step (b), then a liquid in which the prepolymer is sparingly soluble is added, and the resulting solids are recovered by filtering, washing, and drying.

6. A method according to claim 5, wherein said particulate support is silica.

7. A method according to claim 4, wherein the solid is separated from the liquid in step (c) by filtering, then washing the recovered solid with a hydrocarbon, and then drying the washed solid.

8. A method according to claim 7, wherein an alkane is used in the washing.

9. A method according to claim 1, wherein step (a) is conducted in the presence of a particulate support that is insoluble in the liquid being employed in step (a).

10. A method according to claim 9, wherein said particulate support is an inorganic oxide.

11. A method according to claim 4, wherein the prepolymerization involves the prepolymerization of ethylene.

12. A method according to claim 11, wherein the prepolymerization involves the prepolymerization of a mixture of ethylene and 1-butene.

13. A method according to claim 1, wherein step (a) is conducted in the presence of a bridged metallocene having olefinic unsaturation in a branch extending outwardly from the bridge, the ligand of said metallocene having the formula

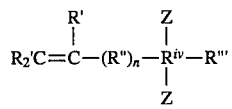

wherein n is 1 or 0; $R^{iv}$ is Si, Ge, C, or Sn; each R' is individually selected from the group consisting of hydrogen and hydrocarbyl radicals having 1 to 10 carbons; R" is selected from the group consisting of hydrocarbyl diradicals containing 1 to 10 carbons; R''' is selected from the group consisting of hydrogen or hydrocarbyl groups containing 1 to 10 carbons; and each Z is the same or different and is selected from the group consisting of substituted or unsubstituted cyclopentadienyl, indenyl, tetrahydroindenyl, and fluorenyl radicals.

14. A method according to claim 13, wherein 5-(9-fluorenyl)- 5-(cyclopentadienyl)-hexene-1 zirconium dichloride is employed.

15. A method according to claim 1, wherein the metallocene is selected from the group consisting of 5-(cyclopentadienyl)-5-(9-fluorenyl)-1 -hexene zirconium dichloride, bis(9-fluorenyl)(methyl)(vinyl)silane zirconium dichloride, bis(9-fluorenyl)(methyl)(prop-2-enyl)silane zirconium dichloride, bis(9-fluorenyl) (methyl)(but-3-enyl)silane zirconium dichloride, bis(9-fluorenyl) (methyl) (hex-5-enyl) silane zirconium dichloride, bis(9-fluorenyl) (methyl)(oct-7-enyl)silane zirconium dichloride, (cyclopentadienyl)(1-allylindenyl) zirconium dichloride, bis(1-allylindenyl) zirconium dichloride, (9-(prop-2-enyl) fluorenyl)(cyclopentadienyl) zirconium dichloride, (9-(prop-2-enyl)(fluorenyl)(pentamethylcyclopentadienyl) zirconium dichloride, bis(9-(prop-2-enyl)fluorenyl) zirconium dichloride, (9-(cyclopent2-enyl)fluorenyl)(cyclopentadienyl) zirconium dichloride, bis(9-(cyclopent-2-enyl)fluorenyl) zirconium dichloride, 5-(2-methylcyclopentadienyl)-5-(9-fluorenyl)- 1-hexene zirconium dichloride, 5-(fluorenyl)- 5-(cyclopentadienyl)-1-hexene hafnium dichloride, (9-fluorenyl)( 1-allylindenyl)dimethylsilane zirconium dichloride, 1-(2,7-di(alphamethylvinyl)-(9- fluorenyl)-1-(cyclopentadienyl)-1,1 -dimethylmethane zirconium dichloride, and 1-(2,7-di(cyclohex-1-enyl) 9-fluorenyl))- 1-(cyclopentadienyl)-1,1-methane zirconium dichloride.

16. A method according to claim 1, wherein two different metallocenes are present during the prepolymerization.

17. A method according to claim 16, wherein at least two different metallocenes each having at least one olefinically unsaturated substituent are employed during the prepolymerization.

18. A method according to claim 17, wherein at least one of the metallocenes is 5-(fluorenyl)-5-(cyclopentadienyl)-hexene- 1 zirconium dichloride.

19. A method according to claim 16, wherein at least two different bridged metallocenes are employed each having olefinic unsaturation in a branch extending outwardly from the bridge.

20. A method for polymerizing an olefin comprising contacting said olefin under suitable polymerization conditions with a solid metallocene-containing catalyst system produced by the process of claim 1.

21. A method according to claim 20 wherein the polymerization is conducted under slurry polymerization conditions.

22. A method according to claim 21 wherein ethylene is polymerized in the presence of an alkane liquid diluent.

23. A method according to claim 22 wherein said solid metallocene-containing catalyst system is prepared from 5-(9-fluorenyl)- 5-(cyclopentadienyl)-hexene- 1 zirconium dichloride.

24. A method according to claim 23 wherein the polymerization is conducted in a continuous loop reactor and isobutane is used as a liquid diluent for the polymerization.

25. A method according to claim 24 wherein the solid metallocene-containing catalyst system used in the polymerization is prepared by (a) combining 5-(9-fluorenyl)-5-(cyclopentadienyl)-hexene-1 zirconium dichloride and methylaluminoxane in a liquid, (b) prepolymerizing ethylene in the resulting liquid, in the presence of silica, and (c) separating the resulting solid from the liquid.

26. A method according to claim 25 wherein the liquid used in step (a) consists essentially of an aromatic liquid.

27. A method according to claim 20 wherein said solid metallocene-containing catalyst system is prepared using at least one bridged metallocene having a vinyl terminated branched bridged ligand of the formula

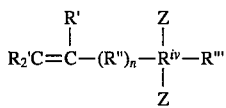

wherein n is 1 or 0; $R^{iv}$ is Si, Ge, C, or Sn; each R' is individually selected from the group consisting of hydrogen and hydrocarbyl diradicals having 1 to 10 carbons; R" is selected from the group consisting of hydrocarbyl radicals containing 1 to 10 carbons; R''' is selected from the group consisting of hydrogen or hydrocarbyl groups containing 1 to 10 carbons; and each Z is the same or different and is selected from the group consisting of substituted or unsubstituted cyclopentadienyl, indenyl, tetrahydroindenyl, octahydrofluorenyl, and fluorenyl radicals.

28. A method according to claim 27 wherein n is 1 and R" is a saturated alkylene diradical having 2 to 10 carbon atoms in its main chain.

29. A method according to claim 28 wherein $R^{iv}$ is C.

30. A method according to claim 28 wherein $R^{iv}$ is Si.

31. A solid metallocene-containing catalyst system produced by the method of claim 1.

32. A solid metallocene-containing catalyst system produced by the method of claim 13.

33. A solid metallocene-containing catalyst system produced by the method of claim 15.

34. A solid metallocene-containing catalyst system produced by the method of claim 14.

35. A solid metallocene-containing composition according to claim 31 further characterized by containing an inorganic support.

36. A method according to claim 1 wherein said liquid catalyst system is formed with at least one metallocene selected from those of the formula $R_x(Z)(Z)MeQ_k$ wherein each Z is bound to Me and is the same or different and is a ligand selected from substituted or unsubstituted cyclopentadienyl, indenyl, tetrahydroindenyl, octahydrofluorenyl, and fluorenyl; R is a structural bridge linking the Z's, and Me is a metal selected from the group consisting of IVB, VB, and VIB metals of the Periodic Table. Each Q is the same or different and is selected from the group consisting of hydrogen, halogen, and organo radicals; x is 1 or 0; k is a number sufficient to fill out the remaining valences of Me, further characterized by the fact that the metallocene has at least one olefinically unsaturated substituent.

37. A method according to claim 36 wherein in the metallocene x is 1 and R includes an olefinically unsaturated substituent.

38. A method according to claim 37 wherein the olefinically unsaturated substituent attached to R has the formula

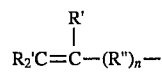

wherein R" is a hydrocarbyl diradical having 1 to 20 carbon atoms; n is 1 or 0, and each R' is individually selected from the group consisting of organo radicals having 1 to 10 carbon atoms and hydrogen.

* * * * *